(12) United States Patent
Boden et al.

(10) Patent No.: US 6,844,302 B1
(45) Date of Patent: Jan. 18, 2005

(54) ENCAPSULATED FLAVOR AND FRAGRANCE

(75) Inventors: Richard M. Boden, Ocean, NJ (US); David Agyemang, Sayreville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 731 days.

(21) Appl. No.: 09/698,828

(22) Filed: Oct. 27, 2000

(51) Int. Cl.[7] .............................. C11D 3/50; C11D 3/32; A61K 7/46
(52) U.S. Cl. ........................ 510/101; 510/501; 512/4
(58) Field of Search ................................ 510/101, 501; 512/4

(56) References Cited

U.S. PATENT DOCUMENTS

| | | | | | |
|---|---|---|---|---|---|
| 3,627,325 A | * | 12/1971 | Breslow | .................. | 273/152.1 |
| 4,493,869 A | * | 1/1985 | Sweeny et al. | ............. | 428/201 |
| 4,528,226 A | * | 7/1985 | Sweeny | ........................ | 428/40 |
| 4,769,390 A | * | 9/1988 | Roelz et al. | ................. | 514/588 |
| 5,211,959 A | * | 5/1993 | Yoshii et al. | ................ | 424/489 |
| 5,709,871 A | * | 1/1998 | Hill | ............................ | 424/409 |
| 5,755,320 A | * | 5/1998 | Weder | ........................ | 206/204 |

OTHER PUBLICATIONS

G. E. Barker et al., Journal of the American Oil Chemists' Society, 1955, vol. 32(5) 249–252. filed May, 1955.*

* cited by examiner

*Primary Examiner*—John Hardee
(74) *Attorney, Agent, or Firm*—Joseph F. Leightner

(57) ABSTRACT

The present invention provides solid complexes of urea and flavor and fragrance chemicals as well as methods of providing the complexes. The complexes are advantageously incorporated in powdered detergent and bleach products. The urea complexes protect the flavor or fragrance molecules from chemical reaction with other elements of the products. When added to water the urea complex is quickly removed from the flavor or fragrance molecule thereby delivering the material at the desired time.

17 Claims, No Drawings

ENCAPSULATED FLAVOR AND FRAGRANCE

FIELD OF THE INVENTION

The present invention is related to flavor and fragrance molecules that are protected by a urea complex. The urea complex prevents the flavor and fragrance molecules from oxidation prior to being released at the desired time.

BACKGROUND OF THE INVENTION

Flavor and fragrance molecules are often placed in environments that adversely effect the stability of the flavor or fragrance. For example, laundry bleaches contain oxidizing agents that can cause a fragrance to oxidize thereby diminishing the delivery of the fragrance at the desired time.

Various approaches have been tried to protect the flavor or fragrance such as encapsulation in various materials such as waxes or polymers. These approaches suffer from the drawback of additional cost of the encapsulating material, additional and costly processing to encapsulate the fragrance or flavor and the need to remove the encapsulating material in an inexpensive and easy manner.

A continuing need exists for a simple, inexpensive method to protect flavor and fragrance materials prior to use, the coating being easily removed when desired.

SUMMARY OF THE INVENTION

The present invention provides a solid complex comprising:
  a substantially linear flavor or fragrance molecule, the flavor or fragrance molecule having a backbone of at least 5 atoms in length; and
  urea wherein the urea provides a protective complex around the substantially linear flavor or fragrance molecule.

The present invention also provides a method for providing a flavor or fragrance molecule with a protective coating comprising:
  providing urea in an amount sufficient to provide a protective coating;
  providing a solvent;
  providing a substantially linear flavor or fragrance molecule having a background of greater than or equally to five molecules;
  admixing said urea, solvent and flavor or fragrance molecule;
  removing said solvent and recovering said flavor or fragrance molecule with protective urea coating.

These and other embodiments of the present invention will be described herein.

DETAILED DESCRIPTION OF THE INVENTION

The present invention is directed to a method for creating a protective urea barrier around a flavor or fragrance molecule. The urea forms a complex that protects the flavor or fragrance molecule. The present invention is well suited to be used in powdered detergents since the flavor and fragrance molecules would be protected by the urea complex until it is placed into water, preferably warm water, which would release the fragrance from the urea complex and impart the fragrance to the clothes. In addition, the urea complex protects the fragrance molecules from oxidizing agents in a detergent, such as bleach, prior to use.

The flavor or fragrance compounds of the present invention are substantially linear, having a minimum chain length of greater or equal to five carbon atoms. More preferably the molecules have a minimum chain length of greater than or equal to five carbon atoms, more preferably greater than or equal to 8 carbon atoms. In the present invention, molecules having longer chain lengths are easily accommodated by the use of higher levels of urea. Shorter molecules, i.e., molecules of $C_2$, $C_3$ and $C_4$ are not viable since these molecules are too short to be successfully complexed by urea. As used in throughout this specification, the term compound contemplates mixtures, combinations of two or more suitable molecules rather than a single material being encapsulated by urea.

The term substantially linear is understood to mean that the backbone does not contain any branches containing three or more atoms, other than hydrogen, off of the main backbone of the molecule. The backbone of the molecule may contain a ring, such as cyclopentane, cyclobutane, cyclohexane as well as aryl rings. The backbone of the molecule may also include epoxy bridges without deviating from the scope of the present invention. Preferably the molecules to be complexed with the urea do not contain any sidechains, however the present invention contemplates less than about 7, preferably less than about 6, preferably less than about 5 sidechains on the molecule. In highly preferred situations, there are fewer than about 4, preferably fewer than about 3 and most preferably fewer than about 2 sidechains on the molecule.

For purposes of explanation, the number of atoms in the backbone of the molecule is set forth in the following examples. As with conventional chemical naming techniques, the longest molecular chain is designated as the backbone. Atoms in the backbone include, but are not limited to, carbon, oxygen, nitrogen, silicon, phosphorous, sodium, potassium, calcium and the like. Hydrogen atoms are not counted among the atoms along the backbone. The sidechains are the atoms that are off of the backbone, i.e., are not part of the longest chain. The following molecules are within the scope of the present invention, the numbers indicting the length of the backbone of the molecule, as well as the length of any side chains:

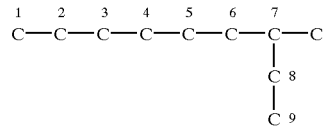

(longest chain length of 9, one side chain of carbon)

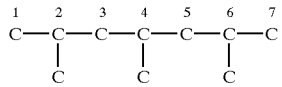

(the penyl ring provides at least one carbon atome of length)

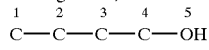

(chain length of 7, 3side chains of 2)

$$\underset{1}{C}-\underset{2}{C}-\underset{3}{C}-\underset{4}{C}-\underset{5}{OH}$$

The oxygen molecule is counted among the atoms of the backbone and provides a chain length of 5 molecules.

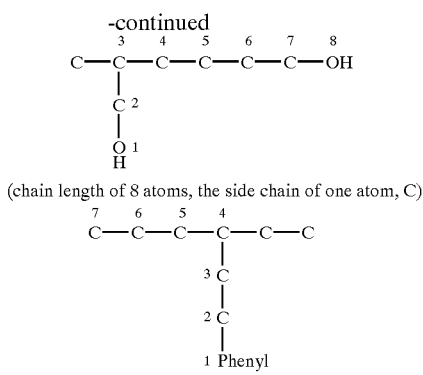

(chain length of 8 atoms, the side chain of one atom, C)

This molecule has a side chain of two atoms. Longest chain is seven atoms including phenyl, at the one position and 2 carbons at the 3 position.

The following molecules are not within the scope of the present invention due to having side chains that render the molecule substantially non-linear:

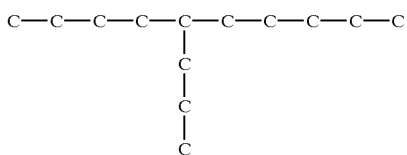

this molecule has a side chain of 3 carbons atoms.

Also not contemplated by the present invention are molecules having attached multiple ring groups, the ring groups can be carbon rings or heterocyclic rings. These attached rings create make the rings too bulk for complexation with urea. For clarity the molecules that contain multiple adjacent attached rings such as found in napthalene and anthracene are outside the scope of the present invention.

Olfactory effective amount is understood to mean the amount of compound in perfume compositions the individual component will contribute its particular olfactory characteristics, but the olfactory effect of the perfume composition will be the sum of the effects of each of the perfume or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

Taste effective amount is understood to mean the amount of compound in compositions the individual component will contribute its particular taste characteristics, but the taste effect of the perfume composition will be the sum of the effects of each of the taste ingredients. Thus the compounds of the invention can be used to alter the taste of the food, or by modifying the taste contributed by another ingredient in the composition. The amount will vary depending on many factors including other ingredients, their relative amounts and the effect that is desired.

The level of flavor or fragrance molecule complexed by urea varies from 0.01 to about 20 weight percent, preferably from about 0.1 to about 10 weight percent, more preferably from about 1.0 to about 5 weight percent of the total composition.

The flavor and fragrance molecules of the present invention are select from the group consisting of $(C_5-C_{12})$alkyl, $(C_5-C_{12})$alkoxy, halo$(C_5-C_{12})$alkyl, halo$(C_5-C_{12})$alkoxy, $(C_{5-C12})$alkenyl, halo$(C_5-C_{12})$alkenyl, $(C_5-C_{12})$alkynyl, halo$(C_5-C_{12})$alkynyl, $(C_5-C_{12})$alkoxy$(C_1-C_{12})$alkyl, $(C_5-C_{12})$alkoxy$(C_2-C_{12})$alkenyl, $(C_1-C_{12})$alkoxy$(C_2-C_{12})$alkynyl, $(C_2-C_{12})$alkenyl$(C_1-C_{12})$alkoxy, $(C_2-C_{12})$alkynyl $(C_1-C_{12})$alkoxy, $(C_2-C_{12})$alkynyl$(C_2-C_{12})$alkenyl, $(C_2-C_{12})$alkenyl$(C_2-C_{12})$alkynyl, $(C_3-C_7)$cycloalkyl, halo $(C_3-C_7)$cycloalkyl, $(C_3-C_7)$cycloalkyl$(C_1-C_{12})$alkyl, $(C_3-C_7)$cycloalkyl$(C_2-C_{12})$alkenyl, $(C_3-C_7)$cycloalkyl $(C_2-C_{12})$alkynyl, $(C_1-C_{12})$alkyl$(C_3-C_7)$cycloalkyl, $(C_1-C_{12})$alkoxy$(C_3-C_7)$cycloalkyl, $(C_2-C_{12})$alkenyl $(C_3-C_7)$cycloalkyl, $(C_2-C_{12})$alkynyl$(C_3-C_7)$cycloalkyl, halo$(C_1-C_{12})$alkyl$(C_3-C_7)$cycloalkyl, halo$(C_1-C_{12})$alkoxy $(C_3-C_7)$cycloalkyl, halo$(C_2-C_{12})$alkenyl$(C_3-C_7)$cycloalkyl, halo$(C_2-C_{12})$alkynyl$(C_3-C_7)$cycloallyl, halo$(C_3-C_7)$alkenyl $(C_3-C_7)$cycloalkyl, $(C_1-C_{12})$alkoxy$(C_1-C_{12})$alkyl$(C_3C_7)$ cycloalkyl, halo$(C_3-C_7)$cycloalkyl$(C_3-C_7)$cycloalkyl, $(C_1-C_{12})$alkoxy$(C_1-C_{12})$alkyl$(C_3-C_7)$cycloalkyl, $(C_1-C_{12})$ alkoxy$(C_2-C_{12})$alkenyl$(C_3-C_7)$cycloalkyl, $(C_2-C_{12})$alkenyl $(C_1-C_{12})$alkoxy$(C_3-C_7)$cycloalkyl, $(C_1-C_{12})$alkoxy $(C_2-C_{12})$alkynyl$(C_3-C_7)$cycloalkyl, $(C_2-C_{12})$alkynyl $(C_1-C_{12})$alkoxy$(C_3-C_7)$cycloalkyl, $(C_2-C_{12})$alkenyl $(C_2-C_{12})$alkynyl$(C_3-C_7)$cycloalkyl, $(C_2-C_{12})$alkynyl $(C_2-C_{12})$alkenyl$(C_3-C_7)$cycloalkyl, $(C_3-C_7)$cycloalkyl $(C_3-C_7)$cylcoalkyl, $(C_1-C_{12})$alkyl$(C_3-C_7)$cycloalkyl $(C_3-C_7)$cycloalkyl, $(C_2-C_{12})$alkenyl$(C_3C_7)$cycloalkyl $(C_3-C_7)$cycloalkyl, $(C_2-C_{12})$alkynyl$(C_3-C_7)$cycloalkyl $(C_3-C_7)$cycloalkyl, $(C_1-C_{12})$alkoxy$(C_3-C_7)$cycloalkyl $(C_3-C_7)$cycloalkyl, $(C_3-C_7)$cycloalkyl$(C_1-C_{12})$alkyl $(C_3-C_7)$cycloalkyl, $(C_3-C_7)$cylcoalkyl$(C_2-C_{12})$alkenyl $(C_3-C_7)$cycloalkyl, $(C_3-C_7)$cycloalkyl$(C_2-C_{12})$alkynyl $(C_3-C_7)$cycloalkyl, $(C_3-C_7)$cycloalkyl$(C_1-C_{12})$alkoxy $(C_3-C_7)$cycloalkyl, $(C_3-C_7)$cycloalkyl$(C_3-C_7)$cycloalkyl $(C_3-C_7)$cycloalkyl, $(C_3-C_7)$cycloalkyl$(C_1-C_{12})$alkenyl $(C_3-C_7)$cycloalkyl, $(C_3-C_7)$cycloalkyl$(C_1-C_{12})$alkoxy $(C_2-C_{12})$alkynyl$(C_3-C_7)$cycloalkyl, aryl, aralkyl, aryl $(C_1-C_{12})$alkoxy, aryl$(C_2-C_{12})$alkenyl, aryl$(C_2-C_{12})$alkynyl, aryl$(C_3-C_7)$cycloalkyl, aryloxy$(C_1-C_{12})$alkyl, aryloxy $(C_2-C_{12})$alkynyl, aryloxy$(C_2-C_{12})$alkenyl, aryl$(C_1-C_{12})$ alkoxy$(C_3-C_7)$cycloalkyl, aryl$(C_2-C_{12})$alkenyl$(C_3-C_7)$ cycloalkyl, aryl$(C_2-C_{12})$alkynyl$(C_3-C_7)$cycloalkyl, aryl $(C_3-C_7)$cycloalkyl$(C_3-C_7)$cycloalkyl, $(C_3-C_7)$ cycloalkylaryl, aryl$(C_1-C_4)$alkyl$(C_3-C_7)$cycloalkyl, heterocyclic, aryl$(C_1-C_4)$alkylheterocyclic, aryl$(C_2-C_4)$ alkenylheterocyclic, aryl$(C_2-C_4)$alkynylheterocyclic, heterocyclic$(C_1-C_4)$alkyl, and heterocyclic$(C_3-C_7)$ cycloalkyl, $(C_1-C_6)$alkylphosphinyl, $(C_{-C6})$ alkylphosphonyl, $(C_1-C_6)$alkylphosphonate, $(C_1-C_6)$ alkylphosphite.

The term "alkyl" includes both branched and straight chain alkyl groups from 5 to 12 carbon atoms. Typical alkyl groups are n-pentyl, isopentyl, n-hexyl, n-heptyl, n-octyl, isooctyl, nonyl, decyl, undecyl, dodecyl, n-hexadecyl, n-tetracosyl, n-octacyosanyl and the like. Also included are alkyls with a branch in the chain. For example, those with skill in the art will recognize that there are numerous variations that are possible with any materials listed in this application. For example, included in the present invention are heptanes $(C_7H_{16})$ which include the following molecules n-heptane, 2-methylhexane, 3-methylhexane, 2,2-dimethylpentane, 2,3-dimethylpentane, 2,4-dimethylpentane, 3,3dimethylpentane 3-ethylpentane, 2,2,3-trimethylbutane. The term "haloalkyl" refers to a straight or branched alkyl group substituted with 1 to 3 halogens.

The term "alkoxy" includes both branched and straight chain alkyl groups from 1 to 12 carbon atoms containing at least one oxygen atom. Typical alkoxy groups are n-pentoxy, isopentoxy, n-hexoxy, n-heptoxy and the like. The term "haloalkoxy" refers to an alkoxy group substituted with 1 to 3 halogens.

The term "alkenyl" refers to an ethylenically unsaturated hydrocarbon group, straight or branched, having a chain length of 5 to 12 carbon atoms and 1 to 2 ethylenic bonds. The term "haloalkenyl" refers to an alkenyl group substituted with 1 to 3 halogen atoms.

The term "alkynyl" refers to an unsaturated hydrocarbon group, straight or branched, having a chain length of 5 to 12 carbon atoms and 1 to 2 acetylenic bonds. The term "halokynyl" refers to an alkynyl group substituted with 1 to 3 halogens.

The term "cycloalkyl" refers to a saturated ring system having 3 to 7 carbon atoms.

The term "aryl" includes phenyl or napthyl, which may be substituted with up to three substituents independently selected from the group consisting of halogen, cyano, nitro, phenyl, phenoxy, ($C_1$–$C_6$)alkyl, ($C_1$–$C_4$)alkylthio, ($C_1$–$C_4$) alkylsulfoxide, ($C_1$–$C_6$)alkoxy, and halo ($C_1$–$C_4$) alkyl.

Typical aryl substituents include, but are not limited to, 4-chlorophenyl, 4-fluorophenyl, 4-bromophenyl, 2-methoxyphenyl, 2-methylphenyl, 3-methylphenyl, 4-methylphenyl, 2,4-dibromophenyl, 3,5-difluorophenyl, 2,4,6-trichlorophenyl, 4-methoxyphenyl, 2-chloronapthyl, 2,4-dimethoxyphenyl, 4-(trifluoromethyl)phenyl and 2-iodo-4-methylphenyl.

The term "heterocyclic" refers to a substituted or unsubstituted 5 to 6 membered unsaturated ring containing one, two or three heteroatoms, preferably one or two heteroatoms independently selected from oxygen, nitrogen and sulfur, or to a bicyclic unsaturated ring system containing up to 10 atoms including one heteroatom selected from oxygen, nitrogen and sulfur. Examples of heterocycles include, but are not limited to, 2-, 3-, or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from ($C_1$–$C_2$) alkyl, halogen, cyano, nitro and trihalomethyl.

The term "aralkyl" is used to describe a group wherein the alkyl chain is from 1 to 10 carbon atoms and can be branched or straight chain, preferably a straight chain, with the aryl portion, as defined above, forming a terminal portion of the aralkyl moiety. Typical aralkyl moieties are optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4dichlorobenzyl, 2,4-dibromobenzyl, 2-methylbenzyl, 3-methylbenzyl and 4-methylbenzyl. Typical phenethyl moieties are 2-(chlorophenyl)ethyl, 2-(3-chlorophenyl) ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-phenyl)ethyl, 2-(4-methylphenyl) ethyl, 2-(4-trifluoromethylphenyl)ethyl, 2-(2methoxyphenyl)ethyl, 2-(3-methoxyphenyl)ethyl, 2-(4-methoxyphenyl)ethyl, 2-(2,4-dichlorophenyl)ethyl, 2-(3,5-methoxyphenyl)ethyl. Typical phenpropyl moieties are 3-phenylpropyl, 3-(2-chlorophenyl)propyl, 3-(3-chlorophenyl)propyl, 3-(4-chlorophenyl)propyl, 3-(2,4-dichlorophenyl)propyl, 3-(2-fluorophenyl)propyl, 3-(3-fluorophenyl)propyl, 3-(4-fluorophenyl)propyl, 3(2-methylphenyl)propyl, 3-(3-methylphenyl)propyl, 3-(4-methylphenyl)ethyl, 3-(2-methoxyphenyl)propyl, 3-(3-methoxyphenyl)propyl, 3-(4-methoxyphenyl)propyl, 3-(4-trifluoromethylphenyl)propyl, 3-(2,4-dichlorophenyl)propyl and 3-3,5dimethoxyphenyl) propyl.

Typical phenbutyl moieties include 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl) butyl, 4-(4-fluorophenyl) butyl, 4-(2-methylphenyl)butyl, 4-(3-methylphenyl)butyl, 4-(4-methylphenyl)butyl, 4-(2,4-dichlorophenyl)butyl, 4-(2-methoxyphenyl)butyl, 4-(3-methoxyphenyl)butyl and 4-(4-methoxyphenyl) butyl.

Halogen or halo is meant to include iodo, fluoro, bromo and chloro moieties.

Preferably the molecules encapsulated by urea are linear such as n-octanol, n-dodecanol and the like. The present invention contemplates some branching off of the main backbone. Various atoms may be contained in the flavor or fragrance molecules of the present invention. In addition to hydrocarbons containing carbon and hydrogen, molecules of the present invention may also include other atoms, including but not limited to oxygen, nitrogen, phosphorus and sulfur. The molecules include without limitation, alcohols, esters, aldehydes, acids and hydrocarbons.

The following materials are commercially available fragrance materials available from International Flavors & Fragrances Inc., Hazlet, N.J. Suitable alcohols include, but are not limited to:

| NAME | COMMON NAME |
| --- | --- |
| 10-Undecen-1-ol | ALCOHOL C-11 UNDECYLENIC |
| Alpha-n-Amyl Cinnamyl Alcohol | AMYL CINNAMIC ALCOHOL |
| 1-Octen-3-ol | AMYL VINYL CARBINOL |
| Para-Methoxy Benzyl Alcohol | ANISIC ALCOHOL |
| Alpha-3,3-Trimethyl Cyclohexane-1-Methanol | APHERMATE |
| Para-Isopropyl Cyclohexanol | APO PATCHONE |
| 2-Ethyl-4-(2,2,3-Triethyl-3-Cyclopenten-1-yl-2-Buten-1-ol | BACDANOL |
| 3,7-Dimethyl-6-Octen-1-ol | CITRONELLOL COEUR |
| Phenoxy Acetaldehyde | CORTEX ALDEHYDE |
| Para-Cymen-7-ol | CUMINYL ALCOHOL |
| 3,7-Dimethyl-6-Octen-3-ol | DIHYDRO LINALOOL |
| 3,7-Dimethyl-1-Octanol | DIMETHYL OCTANOL |
| 2-Methyl-4-Phenyl-2-Butanol | DIMETHYL PHENYL ETHYL CARBINOL |
| 2,4-Dimethyl-3-Cyclohexene-1-Methanol | FLORALOL |
| 3,7-Dimethyl-2,6-Octadien-1-ol | GERANIOL ABSOLUTE |
| O,m,p-Methyl Phenyl Ethanol | HAWTHANOL |
| 3-Hexen-1-ol | HEXENOL |
| Beta-Methyl Phenyl Ethyl Alcohol | HYDRATROPIC ALCOHOL COEUR |
| 3,7-Dimethyl-1,7-Octanediol | HYDROXYOL |
| Alpha-Isobutyl Phenethyl Alcohol | ISOBUTYL BENZYL CARBINOL |
| 3,4,5,6,6-Pentamethyl-2-Heptanol | KOHINOOL |
| 2,6,-Dimethyl Heptan-6-ol | LOLITOL |
| 2,6-Dimethyl-7-Octen-2-ol | LYMOLENE |
| 5-(2,6,6-Triethyl-2-Cyclohexen-1-yl)-4-Penten-3-one | ALPHA METYYL IONONE |
| 3-Methyl-4-2,6,6-Trimethyl-1-Cyclohexen-1-yl)-3-Buten-2-one | DELTA METHYL IONONE |
| 2,6-Dimethyl-3,5-Octadien-2-ol | MUGUOL |
| 2-Methyl-6-Methylene-7-Octen-2-ol | MYRCENOL |
| 3,7-Dimethyl-2,6-Octadien-1-ol | NEROL |
| 2,6-Dimethyl-5,7-Octadien-2-ol | OCIMENOL |
| alpha,alpha-4-Trimethyl Benzene Ethanol | PARA METHYL DIMETHYL BENZYL CARBINOL |
| 4-Tertiary Butyl Cyclohexanol | PATCHONE |
| 3-Methyl-5-Phenyl-1-Petntanol | PHENOXANOL |

-continued

| NAME | COMMON NAME |
|---|---|
| 2-Benzyl-M-Dioxan-5-ol | PHENYL ACETALDEHYDE GLYCERINE ACETAL |
| 2-Phenyl Ethyl Alcohol | PHENYL ETHYL ALCOHOL |
| 3-Methyl-1-Phenyl-3-Pentanol | PHENYL ETHYL METHYL ETHYL CARBINOL |
| 3,7-Dimethyl-6-Octen-1-ol | RHODINOL COEUR |
| 9-Decen-1-ol | ROSALVA |
| alpha,lpha-4-Trixnethyl-3-Cyclo-hexene-1-Methanol | ALPHA TERPINEOL |
| 3,7-Dimethyl-3-Octanol | TETRAHYDRO LINALOOL |
| 2,6-Dimethyl-2-Octanol | TETRAHYDRO MYRCENOL |
| 2-Tertiary-Butyl Cyclohexanol | VERDOL |

Suitable aldehydes include, commercially available as a fragrance, but are not limited to:

| NAME | COMMON NAME |
|---|---|
| 1-Octanal | ALDEHYDE C-8 |
| 1-Nonanal | ALDEHYDE C-9 |
| 1-Decanal | ALDEHYDE C-10 |
| 2-Methyl Decanal | ALDEHYDE C-11 MOA |
| 10-Undecen-1-al | ALDEHYDE C-11 UNDECYLENIC |
| 1-Undecanal | ALDEHYDE C-11 UNDECYLIC |
| 1-Dodecanal | ALDEHYDE C-12 LAURIC |
| 2-Methyl Undecanal Methyl Nonyl Acetaldehyde | ALDEHYDE C-12 MNA |
| alpha-n-Amylcinnamic Alcohol Coeur | AMYL CINNAMIC ALDEHYDE COEUR |
| 3,7-Dimethyl-2-Methylene-6-Octenal | BERGAMAL |
| 2-Methyl-3-(para-Methoxy Phenyl)Propanal | CANTHOXAL |
| 3,7-Dimethyl-2,6-Octadien-1-al | CITRAL |
| 3,7-Dimethyl-2,6-Octadienal Dimethyl Acetal | CITRAL DIMETHYL ACETAL |
| 3,7-Dimethyl-6-Octen-1-al | CITRONELLAL |
| 3,7-Dimethyl-6-Octenyl Methyl Acetal | CITRONELLYL METHYL ACETAL |
| 2-Heptyl-1,3-Dioxolane Octanal Glycol Acetal | CYCLOCTAL |
| Para-Ethyl-alpha,alpha-Dimethyl Hydrocinnamaldehyde | FLORALOZONE |
| 5,9-Dimethyl-4,8-Decadienal | GERALDEHYDE |
| 6,10-Dimethyl-3-oxa-5,9-Undecadien-1-al | PEONY ALDEHYDE |
| Alpha-n-Hexyl Cinnamic Aldehyde | HEXYL CINNAMIC ALDERYDE |
| m-Cymene-7-Carboxaldhyde | HOMOCUMINIC ALDERYDE 50 |
| Ethyl Phenethyl Acetal Acetaldehyde | HYACINTH BODY |
| Phenethyl Propyl Acetal Acetaldehyde | HYACINTH BODY NO. 31 |
| Alpha-Methyl Phenylacetaldehyde | HYDRATROPIC ALDERYDE |
| 7-Hydroxy-3,7-Dimethyl Octanal | HYDROXYCITRONELLAL |
| 10-Undecenal | INTRELEVEN ALDEHYDE |
| Ethyl-cis-3-Hexenyl Acetal Acetaldehyde | LEAF ACETAL EXTRA |
| 3,7-Dimethyl-2,6-Octadien-1-al | LEMSYN |
| 4-(4-Hydroxy-4-Methyl Pentyl)-3-Cyclohexene-1-Carboxaldehyde | LYRAL |
| 2-Methyl-3-Phenyl-2-Propen-1-al | ALPHA-METHYL CINNAMIC ALDEHYDE |
| 2-Methyl Octanal | METHYL HEXYL ACETALDEHYDE |
| 3,7-Dimethyl-6-Octenyl-oxy-Acetaldehyde | MUGUET ALDEHYDE 50 |
| 4-(4-Methyl-3-Pentenyl)-3-Cyclo-hexene-1-Carboxaldehyde | MYRAC ALDEHYDE |
| Alpha-Methyl-4-(1-Methyl Benzene Acetaldehyde | PARA ISOPROPYL HYDRATROPIC ALDEHYDE |
| Dihydro Cinnamic Acetate | PHENYL PROPYL ACETATE |
| 1-Methyl-4-(4-Methyl-3-Pentenyl)-3-Cyclohexene-1-Carboxaldehyde | PRECYCLEMONE B |
| 2,4-Dimethyl-3-Cyclohexene-1-3,5,5-Trimethyl Hexanal | TRIPLAL VANDOR B |
| Para-Methyl Phenoxy Acetaldehyde | XI ALDEHYDE |

Suitable esters, commercially available as a fragrance, include but are not limited to:

| NAME | COMMON NAME |
|---|---|
| 2-Methoxy-4-Propenyl-1)-Phenyl Acetate | ACETYL ISOEUGENOL |
| 2-Pentyloxy-Allyl Ester Glycolic Acid | ALLYL AMYL GLYCOLATE |
| Allyl-n-Hexanoate | ALLYL CAPROATE |
| 3-Cyclohexyl Propionic Acid, Allyl Ester | ALLYL CYCLOHEXYL PROPIONATE |
| Propionate-9-Decen-1-ol | AMBRONATE |
| Isoamyl-n-Butyrate | AMYL BUTYRATE |
| Alpha-n-Amyl Cinnamyl Acetate | AMYL CINNAMIC ACETATE |
| Phenyl Acetic Acid, Isoamyl Ester | AMYL PHENYL ACETATE |
| Isoamyl Propionate | AMYL PROPIONATE |
| Pentyl Ortho Hydroxy Benzoate | AMYL SALICYLATE |
| 2(3)-Methyl Butanoic-1-Acid:2(3)-Methyl Butyl-1-Ester | AMYL VALERATE |
| 1-Octen-3-yl Acetate | AMYL VINYL CARBINYL ACETATE |
| 3-Phenyl-3-Buten-1-yl Acetate | ANISIMAL |
| Para-Methoxy Benzyl Acetate | ANISYL ACETATE |
| Benzyl-n-Butanoate | BENZYL-n-BUTYRATE |
| Formic Acid Benzyl Ester | BENZYL FORMATE |
| Benzyl-3-Methyl Butyrate | BENZYL ISOVALERATE |
| Benzyl-n-Propanoate | BENZYL PROPIONATE |
| Benzyl ortho Hydroxy Benzoate | BENZYL SALICYLATE |
| 3-Phenyl-2-Propen-1-yl Acetate | CINNAMYL ACETATE |
| 3,7-Dimethyl-6-Octen-1-yl Acetate | CITRONELLYL ACETATE |
| 3,7-Dimethyl-6-Octen-1-yl Propionate | CITRONELLYL PROPIONATE |
| 2-Tertiary Pentyl Cyclohexanyl Acetate | CONIFERAN |
| Para-Cymen-7-yl Acetate | CUMINYL ACETATE |
| Cyclohexanethanyl Acetate | CYCLOHEXYLETHYL ACETATE |
| 6-Methyl-3-Isopropenyl Cyclo-hexanyl Acetate | DIHYDRO CARVYL ACETATE |
| Cyclohexane Methanol, 2,4-Dimethyl Acetate | DIHYDRO FLORALATE |
| 2,6-Dimethyl-7-Octen-2-yl Acetate | DIHYDRO MYRCENYL ACETATE |
| alpha,alpha-Dimethyl Phenethyl Acetate | DIMETHYL BENZYL CARBINYL ACETATE |
| alpha,alpha-Dimethyl Phenethyl Butyrate | DIMETHYL BENZYL CARBINYL BUTYRATE |
| alpha,alpha-Dimethyl Phenethyl Isobutyrate | DIMETHYL BENZYL CARBINYL ISOBUTYRATE |
| alpha,alpha-Dimethyl Phenethyl Propionate | DIMETHYL BENZYL CARBINYL PROPIONATE |
| 3,7-Dimethyl-1-Octanyl Acetate | DIMETHYL OCTANYL ACETATE |
| 2-Methyl-4-Phenyl-2-Butyl Acetate | DIMETHYL PHENYL ETHYL CARBINYL ACETATE |
| 2-Methyl-4-Phenyl-2-Butyl Isobutyrate | DIMETHYL PHENYL ETHYL CARBINYL ISOBUTYRATE |
| Ethyl-3-Hydroxy Butyrate | ETHOXIFF |
| n-Butyric Acid Ethyl Ester | ETHYL BUTYRATE |
| n-Hexanoic Acid Ethyl Ester | ETHYL CAPROATE |
| 3,7-Dimethyl-6-Octenyl Ethyl Ester Oxalic Acid | ETHYL CITRONELLYL OXALATE |
| Isovaleric Acid Ethyl Ester | ETHYL ISOVALERATE |
| 3-Methyl-3-Phenyl Glycidic Acid Ethyl Ester | ETHYL METHYL PHENYL GLYCIDATE |
| 2-Methoxy Benzoic Acid Ethyl Ester | ETHYL ORTHO METHOXY BENZOATE |
| 3-Phenyl Glycidic Ethyl Ester | ETHYL-3-PHENYL GLYCIDATE |
| 4-Allyl-2-Methoxy Phenol Acetate | EUGENYL ACETATE |

-continued

| NAME | COMMON NAME |
|---|---|
| 4-Allyl-2-Methoxy Phenyl Phenol Acetate | EUGENYL PHENYL ACETATE |
| 2,4-Dimethyl-3-Cyclohexene-1-Methanyl Acetate | FLORALATE |
| Ethyl-2,4-Dimethyl-1,3-Dioxolane-2-Acetate | FRAISTONE |
| Ethyl-2-Methyl-1,3-Dioxolane-2-Acetate | FRUCTONE |
| Ethyl-2-Hexyl Acetoacetate | GELSONE |
| 3,7-Dimethyl-2,6-Octadien-1-yl Acetate | GERANYL ACETATE |
| 3,7-Dimethyl-2,6-Octadien-1-yl-Butyrate | GERANYL BUTYRATE |
| 3,7-Dimethyl-2,6-Octadien-1-yl Formate | GERANYL FORMATE |
| 3,7-Dimethyl-2,6-Octadien-1-yl Isobutyrate | GERANYL ISOBUTRATE |
| 3,7-Dimethyl-2,6-Octadien-1-yl Propionate | GERANYL PROPIONATE |
| Isobutyric Acid,2,4-Hexadienyl Ester | HEXADIENYL ISOBUTYRATE |
| n-Hexyl Acetate | HEXYL ACETATE |
| n-Hexyl-ortho-Hydroxy Benzoate | n-HEXYL SALICYLATE |
| BETA-Methyl Phenethyl Alcohol Acetate | HYDRATROPYL ACETATE |
| 2-Furanpropionic Acid, Isobutyl Ester | ISOBUTYL FURYL PROPIONATE |
| Phenyl Acetic Acid, Isobutyl Ester | ISOBUTYL PHENYL ACETATE |
| 2H-Pyran-4-ol, Tetrahydro-3-Pentyl Acetate | JASMAL |
| 2H-Pyran-4-ol, 3-Butyltetrahydro-5-Methyl Acetate | JASMELIA |
| 2H-Pyran-4-ol, 3-Butyltetrahydro-5-Methyl Acetate | JESSEMAL |
| Ethyl-3-Hydroxy-3-Phenyl Propionate | LABDANAX |
| Cis-3-Hexenyl Methyl Carbonate | LIFFAROME |
| Anthranillic Acid, Methyl Ester | METHYL ANTHRANILATE |
| 10-Undecenoic Acid, Methyl Ester | METHYL UNDECYLENATE |
| 7-Octen-2-ol, 2-Methyl-6-Methylene Acetate | MYRCENYL ACETATE |
| 2,6-Octadien-1-ol, 3,7-Dimethyl Formate | NERGER FORMATE |
| 2,6-Octadien-1-ol, 3,7-Dimethyl Acetate | NERYL ACETATE |
| Nonyl Alcohol Acetate | NONYL ACETATE |
| 2-Norpinene-2-Ethanol, 6,6-Dimethyl Acetate | NOPYL ACETATE |
| 5,7-Octadien-2-ol, 2,6-Dimethyl Acetate | OCIMENYL ACETATE |
| Lauric Acid Ethyl Ester | OENANTHIC ETHER |
| Octanoic Acid, p-Tolyl Ester | PARA CRESYL CAPRYLATE |
| Isobutyric Acid, p-Tolyl Ester | PARA CRESYL ISOBUTYRATE |
| 4-Methyl Benzene Methanol Acetate | PARA METHYL BENZYL ACETATE |
| 2-Phenoxyethyl Isobutyrate | PHENOXY ETHYL ISOBUTYRATE |
| 2-Phenoxyethyl Propionate | PHENOXYETHYL PROPIONATE |
| 2-Phenyl Ethyl Acetate | PHENYL ETHYL ACETATE |
| 2-Phenyl Ethyl Benzoate | PHENYL ETHYL BENZOATE |
| Beta-Phenyl Ethyl n-Butyrate | PHENYL ETHYL n-BUTYRATE |
| Cinnamic Acid, Phenethyl Ester | PHENYL ETHYL CINNAMATE |
| Phenethyl Alcohol Formate | PHENYL ETHYL FORMATE |
| Beta-Phenyl Ethyl Isobutyrate | PHENYL ETHYL ISOBUTYRATE |
| 3-Pentanol, 3-Methyl-1-Phenyl Acetate | PHENYL ETHYL METHYL ETHYL CARBINYL ACETATE |
| Beta-Phenyl Ethyl Phenyl Acetate | PHENYL ETHYL PHENYL ACETATE |
| Beta-Phenyl Ethyl Propionate | PHENYL ETHYL PROPIONATE |
| Beta-Phenyl Ethyl Salicylate | PHENYL ETHYL SALICYLATE |
| Dihydro Cinnamic Acetate | PHENYL PROPYL ACETATE |
| Dihydro Cinnamic Propionate | PHENYL PROPYL PROPIONATE |
| 2-Buten-1-ol-3-Methyl Acetate | PHENYL ACETATE |
| 2-Buten-1-ol-3-Methyl Benzoate | PROFLORA |
| 6-Octen-1-ol-3,7-Dimethyl Acetate | RHODINYL ACETATE |
| 6-Octen-1-ol-3,7-Dimethyl Butyrate | RHODINYL BUTYRATE |
| 6-Octen-1-ol-3,7-Dimethyl Formate | RHODINYL FORMATE |
| 6-Octen-1-ol-3,7-Dimethyl Isobutyrate | RHODINYL ISOBUTYRATE |
| Cyclohexane-1-Methanol, alpha, 3,3-Trimethyl Acetate | ROSAMUSK |
| 9-Decen-1-yl Acetate | ROSEATE |
| Methyl Phenyl Carbinyl Acetate | STYRALYL ACETATE |
| Methyl Phenyl Carbinyl Propionate | STYRALYL PROPIONATE |
| 3-Cyclohexene-1-Methanol, alpha, alpha, 4-Trimethyl Acetate | TERPINYL ACETATE |
| 3-Octanol, 3,7-Dimethyl-2-Octanol, 2,6-Dimethyl Acetate | TETRAHYDRO MUGYL ACETATE |
| 3,55-Trimethyl Hexyl Acetate | VANORIS |
| 3,6-Dimethyl-beta-Resorcyclic Acid Methyl Ester | VERAMOSS |
| 2-Tertiary-Butyl-Cyclohexanyl Acetate | VERDOX |
| Cis-3-Hexenyl Acetate | VERDURAL EXTRA |
| Cis-3-Hexen-1-yl Isobutyrate | VERDURAL B EXTRA |
| Para-Tertiary-Butyl-Cyclohexyl Acetate | VERTENEX |
| 2-Methyl Butyl Salicylate | ISOAMYL SALICYLATE |
| n-Amyl Salicylate | PENTYL SALICYLATE |

Suitable ketones include, commercially available as a fragrance, but are not limited to:

| NAME | COMMON NAME |
|---|---|
| Para-Methoxy Acetophenone | ACETANISOLE |
| 2-n-Heptyl Cyclopentanone | FLEURAMONE |
| Allyl alpha-Ionone | HEXALON |
| 4-(2,6,6-Trimethyl-1-Cyclohexen-1-yl)-3-Buten-2-one | IONONE |
| 2,3,6-Trimethyl Cyclohexen-4-yl-1-Methyl Ketone | METHYL CYCLO CITRONE |
| 4-(2,4,6-Trimethyl-4-Cyclohexen-1-yl)3-Buten-2-one | IRITONE |
| 3-Methyl-4-(2,6,6-Trimethyl-2-Cyclohexen-1-yl)-3-Buten-2-one | GAMMA METHYL IONONE A |
| 5-(2,6,6-Trimethyl-2-Cyclohexen-1-yl)-4-Buten-3-one | n-METHYL IONONE |
| 3-(HydroxyMethyl)-2-Nonanone | METHYL LAVENDER KETONE |
| 4-Tertiary Pentyl-Cyclohexanone | ORIVONE |
| 4-(para-Hydroxy Phenyl)-2-Butanone | OXYPHENYLON |
| 4-(1,1-Dimethylethyl)-Cyclohexanone | PARA TERTIARY BUTYL CYCLOHEXANONE |
| Gamma-Undecalactone | PEACH ALDEHYDE COEUR |
| Ortho-Tertiary-Butyl-Cyclohexanone | VERDONE |

Other suitable materials include, commercially available as a fragrance, but are not limited to:

| NAME | COMMON NAME |
|---|---|
| Para-Methoxy-alpha-Phenyl Propene | ANETHOLE |
| Methyl, N-3,7-Dimethyl-7-Hydroxy Octylidene Anthinilate | AURALVA |
| 1-Benzyloxy-2-Methoxy-4-Propenyl Benzene | BENZYL ISOEUGENOL |
| 3,7-Dimethyl-2,6-Octadiene-1-Nitrile | CITRALVA |
| 3,7-Dimethyl-6-Octenenitrile | CITRONALVA CITRONAMA |

-continued

| NAME | COMMON NAME |
|---|---|
| 2-Hexyl-1,3-Dioxolane | CITROTONE B |
| n-Dodecane Nitrile | CLONAL |
| 5-Phenyl-5-Methyl-3-Hexanone | 4-DAMASCOL |
| n-Decyl Vinyl Ether | DECAVE |
| n-Decanyl Methyl Ether | DECYL METHYL ETHER |
| di-n-Butyl Sulfide | DIBUTYL SULFIDE |
| 6-Methyl-2-[4-(4-Methyl-3-Pentenyl)-3-Cyclohexen-1-yl]-1,5-Heptadiene | DIMYRCENE |
| Methyl-n-Hexyl Ether | DIOLA |
| 4-Allyl-2-Methoxy Phenol | EUGENOL |
| 3,7-Dimethyl-2,6-Octadien-1-Ethoxy | GERANYL ETHYL ETHER |
| 2-(1-Phenylethyl)-1,3-Dioxolane | HYDRATROPIC ALDEHYDE CYCLOGLYCOL ACETAL |
| 7-Hydroxy-3,7-Dimethyl, Dimethyl Acetal Octanol | HYDROXYCITRONELLAL DIMETHYL ACETAL |
| Acetyl Diisoamylene | KOAVONE |
| p-Mentha-1,8-Diene | D-LIMONENE |
| 4-(4,8-Dimethyl-3,7-Nonadienyl) Pyridine | MARITIMA |
| Methyl Phenethyl Ether | METHYL PHENYL ETHYL ETHER |
| 3,7-Dimethyl-1,3,6-Octatriene | OCIMENE |
| 1,1-Dimethoxy Octane | OCTACETAL |
| p-Menth-1-en-8-yl Methyl Ether | ORANGE FLOWER ETHER |
| Cyclohexyl Phenethyl Ether | PHENAFLEUR |
| 2-Methyl-2-Pentenoic Acid | STRAWBERIFF |
| Cycloglycol Acetal-2-Ethyl Hexanal | SYVERTAL |

In addition to fragrance materials, the present invention is also useful to provide a urea complex around materials used as flavors. Suitable favors include but are not limited to the following materials, also commercially available from International Flavors and Fragrances Inc. The flavors include, citronellal, 1,3,5-undecatriene, methyl nonyl acetaldehyde, citronellol, iso-propyl hexate, hexyl iso-pentanoate, octyl formate, cis-6 nonenal, gamma-methyl-gamma-n-hexyl butyrolactone, n-hexanol, ethyl caprylate, ethyl decylate, heptaldehyde glyceral acetal, cis-4-decenal, tetrahydro linalool, gamma decalatone, hexenal, hexanal, methyl-n-amyl ketone, dodecalactone, massoia lactone, 2-decenal, 4-methyl octanoic acid, 4-methyl-nonanoic acid, capric acid, furfuryl octanoate, DITHALFAROME-705, DITHALFAROME-702, 3-methyl-thio-1-hexanol, octyl butyrate, cis-6-nonenal, dipropyl ketone, 2-ethyl-2-octenoate, capryl alcohol, undecyclic C11 aldehyde, ethyl-2,4-decadienoate, 2ethyl hexanoic acid, 3-hexenyl hexate, 2-heptanol, di-iso-butyl ketone, 2-octen-4-one, 2-butyl-2-butenal, octanal, heptanoic acid, 2-octenal, ethyl butyl ketone, amyl vinyl carbinol, citronello, AMARYLLIDE, delta-undecalactone, OXAROME-722, methyl-2-nonenoate, C-18 aldebyde, Peach ALDEHYDE COEUR, gamma dodecalactow, C-12 aldehyde, C-10 aldehyde, para cresyl caprylate, 2,4-decadienal, heptyl acetate, citronellyl formate, methyl caprylate, methyl nonyl ketone, glyceral acetal heptaldehyde, 2-nonenal, 2,4-undecadienal, methyl undecyl ketone, delta tetradecalactone, ethyl-3-hydroxy hexanoate, cis-6-nonenal, methyl heptyl ketone, ethyl amyl ketone, n-butyl caproate, acetyl n-butyryl, diethyl sebacate, lauric alcohol, methyl hexyl ketone, 3-hexanone, octyl alcohol, phenyl ethyl octanoate, methyl nonylate, rhodinyl acetate, ethyl palmitate, allyl caproate, hexyl butyrate, nonyl acetate, ethyl caproate, ethyl heptoate, linoleic acid, methyl laurate, 2,4-decadienal, ethyl myristate, hexyl propyl rioonate, 2-ethyl hexanol, linoleic acid, methyl hexyl acetaldehyde, iso propyl myristate, n-undecane, n-tridecane, n-pentadecane, n-hexadecane, n-heptadecane, phenyl ethyl hexate, JESSAMAL COER, hexyl cinnarnic aldehyde, methyl heptylate, hexyl caproate, C-10 alcohol, oenathic ether, C-9 aldehyde, C-8 aldehyde, C-7 alcohol, decanyl acetate, methyl nonylenate, amyl caproate, ethyl-2-4-decadienoate, methyl heptin carbonate, hexenyl caproate, ethyl-2-octenoate, ethyl undecanoate, methyl octin carbonate, C-6 acetaldehyde, 2-octenal, FLEXOL, caproic acid, n-hexyl-2-methyl butyrate, INTRELEVEN alcohol, C-12 acetaldehyde, allyl caprylate, 3,4-hexanedione, allyl heptoate, iso-butyl caproate, octyl phenyl acetate, BUTTER DERIVED ACIDS, amyl caprylate, ethyl stearate, C-9 alcohol, pelargonic acid, ALDO MO, n-hexyl isobutyrate, caprylic acid, methyl myristate, RHODINYL butyrate, RHODINYL isobutyrate, 2-decenal, trans4-decenoic acid, lauric acid, amyl caproate, EMPLEX PATCO, hexyl caprylate, methyl caproate, beta, gamma hexenyl formate, MIGLYOL-812 DYNAMIT, 2,4-undecadienal, 1-al-2-tridecene, ORRIS aldehyde, acetyl-isovaleryl, VEGACID 1520, cis4-decenal, ethyl oleate, ethyl-24-decadienoate, n-heptyl-isobutyrate, amyl caprylate, octyl isobutyrate, FRUCTOSE A.I.D, magnesium stearate, 2-nonenal, BIOTIN, Vitamin A palmitate.

The molecules that are encapsulated in the present invention can contain double and triple bonds. Those with skill in the art will appreciate that double bonds within the molecules create various isomers. While complexation of both cis and trans isomers are contemplated by the present invention, trans isomers are preferred in the use of the invention.

The present invention is advantageously used in environments where higher pH conditions are found, pHs such as detergents. Additionally problematic with detergents materials is the inclusion of oxidizing agents such as bleach, which cause fragrance materials to prematurely oxidize thereby reducing or eliminating the fragrance.

The urea is complexed by first dissolving in a suitable solvent. Alcohol can be used to dissolve the urea, with methanol being preferred. After the urea is dissolved in the solvent, the dissolution enhanced by heating of the solvent, the flavor or fragrance molecule is added to solution. The molecule, urea and solvent mixture is allowed to cool to room temperature and the solid material containing the urea/molecule is filtered off. If a solid material is not obtained, cooling means is employed such as packing he reactor contents in ice. In an alternative embodiment of the invention the solvent can be evaporated, providing the urea/molecule complex as a residue.

Once the solid material is obtained, the particle size of the complex can be obtained by grinding techniques that are well known in the art, such as hammermill, cryogenic grinding and the like. The present invention allows the flavor/fragrance urea complex to be of similar size to the detergent or bleach compounds that it is incorporated into.

In the present invention a complexation amount of urea is provided to encapsulate the molecule. The amount of urea required will depend on the length of the molecule to be complexed in the urea. Generally, the level of urea required is at least about 5 moles of urea per mole of fragrance or flavor for each atom in the backbone of the molecule. More preferably about 6 to about 10 moles of urea are used, most preferably from about 6.5 to about 9.0 moles of urea per molecule in the backbone of the molecule.

The present invention provides several advantages, including the instant release of the flavor or fragrance molecule from the urea complex upon addition to an aqueous environment. This feature makes the present invention well suited for use in powdered materials including cleaning products such as detergents, bleaches, fabric softeners and other materials that are routinely added to water. Other applications of the invention include air fresheners, bathroom deodorizers, and the like wherein exposure to moisture in the atmosphere will remove the urea thereby releasing the fragrance. In addition, the present invention can be used to protect flavors that are incorporated in powdered drinks that are added to water, or items that are to be swallowed wherein the moisture in the mouth and digestive system will release the material.

In addition, urea is a common, inexpensive material and the complexation of urea with the flavor and fragrance molecules is easily processed once added to water.

The following examples are provided as specific embodiments of the present invention. Other modifications of the invention will be readily apparent to those skilled in the art without departing from the scope or spirit of the invention. As used herein all percentages are weight percent unless otherwise noted and g is understood to be grams.

EXAMPLE 1

Aldehyde/Urea Inclusion Complex

A three liter reaction flask equipped with a reflux condenser, additional funnel was charged with urea (400 g, 6.67 moles) and 1800 grams of methanol. The urea/methanol mixture was heated to reflux to dissolve the urea in the methanol. The heat was removed and ulenic aldehyde (90 g/0.54 moles) was charged to the reactor. The contents of the reactor were allowed to cool to room temperature providing a precipitate. The precipitate material was then filtered and dried providing a urea/ulenic aldehyde complex.

EXAMPLE 2

The efficacy of urea complexed materials was tested in a laundry detergent. The following samples were prepared which contained percarbonate.

The following materials were prepared using a standard detergent base to simulate a commercially available laundry detergent. Samples were prepared using $C_{12}$ lauric aldehyde, $C_{11}$ undecyclic aldehyde, as well as urea inclusion complexes of $C_{12}$ lauric aldebyde, $C_{11}$ undecyclic aldehyde.

The complexes contained 22% raw material ($C_{12}$ lauric aldehyde, $C_{11}$ undecyclic aldehyde). The samples included the following:

Detergent base plus 0.2% aldehyde $C_{12}$

Detergent base plus 0.2% aldehyde $C_{12}$ urea complex

Detergent base plus 0.2% aldehyde $C_{11}$

Detergent base plus 0.2% aldehyde $C_{11}$ urea complex

The samples were stored at 5° C., room temperature and at 37° C. and 70% relative humidity. After two and four weeks of storage, the detergents were used in standard wash tests conducted using 40° C. and 60° C. with the samples stored at 37° C. A full washload (2.8 kilograms) was washed with 80 grams of detergent powder placed inside the washing machine. The samples were tested for their odor after being placed in water.

The following results were obtained:

| Storage Time | Temperature | Sample and Results $C_{12}$ v $C_{12}$ complex | $C_{11}$ v $C_{11}$ complex |
|---|---|---|---|
| 2 weeks | 40° C. | No difference noted | $C_{11}$ complex performed better |
|  | 60° C. | $C_{12}$ complex performed better | No difference noted |
| 4 weeks | 40° C. | $C_{12}$ complex performed better | $C_{11}$ complex performed better |
|  | 60° C. | $C_{12}$ complex performed better | $C_{11}$ complex performed better |

All of the complexed materials performed at least as well as the aldehyde materials. A more significant fragrance was noted with the samples stored for four weeks, especially with the $C_{11}$ complex washed at 60° C.

What is claimed is:

1. A solid complex consisting of:
   a substantially linear flavor or fragrance molecule, the flavor or fragrance molecule having a backbone of at least 5 atoms in length;
   solvent; and
   urea wherein the urea provides a protective complex around the substantially linear flavor or fragrance molecule.

2. A solid complex consisting of:
   a substantially linear flavor or fragrance molecule, the flavor or fragrance molecule having a backbone of at least 5 atoms in length; and
   urea wherein the urea provides a protective complex around the substantially linear flavor or fragrance molecule.

3. The solid complex of claim 1 or 2 wherein the urea is provided in an amount of greater than or equal to 5 moles of urea per mole of fragrance or flavor for each atom in the backbone of the flavor or fragrance molecule.

4. The solid complex of claim 1 or 2 wherein the substantially linear flavor or fragrance molecule is selected from the group consisting of aldehyde, ketone and acid.

5. The solid complex of claim 1 or 2 wherein the flavor or fragrance is selected from the group consisting of 1-octanal, 1-nonanal, 1-decanal, 2-methyl decanal, 10-undecen-1-al, 1-undecanal, 1-dodecanal, 2-methyl undecanal methyl nonyl acetaldehyde, alpha-n-amylcinnamic alcohol coeur, 3,7-dimethyl-2-methylene-6-octenal, 2-methyl-3-(para-methoxy phenyl)-propanal, 3,7-dimethyl-2,6-octadien-1-al, 3,7-dimethyl-2,6-octadienal dimethyl acetal, 3,7-dimethyl-6-octen-1-al, 3,7-dimethyl-6-octenyl methyl acetal, 2-heptyl-1,3-dioxolane octanal glycol acetal, para-ethyl-alpha,alpha-dimethyl hydrocinnamaldehyde, 5,9-dimethyl-4,8-decadienal, 6,10-dimethyl-3-oxa-5,9-undecadien-1-al, alpha-n-hexyl cinnamic aldehyde, m-cymene-7-carboxaldehyde, ethyl phenethyl acetal acetaldehyde, phenethyl propyl acetal acetaldehyde, alpha-methyl phenylacetaldehyde, 7-hydroxy-3,7-dimethyl octanal, 10-undecenal, ethyl-cis-3-hexenyl acetal acetaldehyde, 3,7-dimethyl-2,6-octadien-1-al, 4-(4-hydroxy-4-methyl pentyl)-3-cyclohexene-1-carboxaldehyde, 2-methyl-3-phenyl-2-propen-1-al, 2-methyl octanal, 3,7-dimethyl-6-octenyl-oxy-acetaldehyde, 4-(4-methyl-3-pentenyl)-3-cyclohexene-1-carboxaldehyde, alpha-methyl-4-(1-methyl benzene acetaldehyde, dihydro cinnamic acetate, 1-methyl-4-(4-methyl-3-pentenyl)-3-cyclohexene-1-carboxaldehyde, 2,4-dimethyl-3-cyclohexene-1-carboxaldehyde, 3,5,5-trimethyl hexanal, and para-methyl phenoxy acetaldehyde.

6. The solid complex of claim 1 or 2 wherein the flavor or fragrance is selected from the group consisting of para-methoxy acetophenone, 2-n-heptyl cyclopentanone, allyl alpha-ionone, 4-(2,6,6-trimethyl-1-cyclohexen-1-yl)-3-buten-2-one, 2,3,6-trimethyl cyclohexen-4-yl-1-methyl ketone, 4-(2,4,6-trimethyl-4-cyclohexen-1-yl)3-buten-2-one, 3-methyl-4-(2,6,6-trimethyl-2-cyclohexen-1-yl)-3-buten-2-one, 5-(2,6,6-trimethyl-2-cyclohexen-1-yl)-4-buten-3-one, 3-(hydroxymethyl)-2-nonanone, 4-tertiary pentyl-cyclohexanone, 4-(para-hydroxy phenyl)-2-butanone, 4-(1,1-dimethylethyl)-cyclohexanone, gamma-undecalactone, and ortho-tertiary-butyl-cyclohexanone.

7. The solid complex of claim 1 or 2 wherein the flavor or fragrance is selected from the group consisting of 2-methoxy-4-(propenyl-1)-phenyl acetate, 2-pentyloxy-allyl ester glycolic acid, allyl-n-hexanoate, 3-cyclohexyl propionic acid, allyl ester, propionate-9-decen-1-ol, isoamyl-n-butyrate, alpha-n-amyl cinnamyl acetate, phenyl acetic acid, isoamyl ester, isoamyl propionate, pentyl ortho hydroxy benzoate, 2(3)-methyl butanoic-1-acid, 2(3)-methyl butyl-1-ester, 1-octen-3-yl acetate, 3-phenyl-3-buten-1-yl acetate, para-methoxy benzyl acetate, benzyl-n-butanoate, formic acid benzyl ester, benzyl-3-methyl butyrate, benzyl-n-propanoate, benzyl ortho hydroxy benzoate, 3-phenyl-2-propen-1-yl acetate, 3,7-dimethyl-6-octen-1-yl acetate, 3,7-dimethyl-6-octen-1-yl propionate, 2-tertiary pentyl cyclohexanyl acetate, para-cymen-7-yl acetate, cyclohexanethanyl acetate, 6-methyl-3-isopropenyl cyclohexanyl acetate, cyclohexane methanol, 2,4-dimethyl acetate, 2,6-dimethyl-7-octen-2-yl acetate, alpha,alpha-dimethyl phenethyl acetate, alpha,alpha-dimethyl phenethyl butyrate, alpha,alpha-dimethyl phenethyl isobutyrate, alpha,alpha-dimethyl phenethyl propionate, 3,7-dimethyl-1-octanyl acetate, 2-methyl-4-phenyl-2-butyl acetate, 2-methyl-4-phenyl-2-butyl isobutyrate, ethyl-3-hydroxy butyrate, n-butyric acid ethyl ester, n-hexanoic acid ethyl ester, 3,7-dimethyl-6-octenyl ethyl ester oxalic acid, isovaleric acid ethyl ester, 3-methyl-3-phenyl glycidic acid ethyl ester, 2-methoxy benzoic acid ethyl ester, 3-phenyl glycidic ethyl ester, 4-allyl-2-methoxy phenol acetate, 4-allyl-2-methoxy phenyl phenol acetate, 2,4-dimethyl-3-cyclohexene-1-methanyl acetate, ethyl-2,4-dimethyl-1,3-dioxolane-2-acetate, ethyl-2-methyl-1,3-dioxolane-2-acetate, ethyl-2-hexyl acetoacetate, 3,7-dimethyl-2,6-octadien-1-yl acetate, 3,7-dimethyl-2,6-octadien-1-yl-butyrate, 3,7-dimethyl-2,6-octadien-1-yl formate, 3,7-dimethyl-2,6-octadien-1-yl isobutyrate, 3,7-dimethyl-2,6-octadien-1-yl propionate, isobutyric acid, 2,4-hexadienyl ester, n-hexyl acetate, n-hexyl-ortho-hydroxy benzoate, beta-methyl phenethyl alcohol acetate, 2-furanpropionic acid, isobutyl ester, phenyl acetic acid, 2H-pyran-1-ol, tetrahydro-3-pentyl acetate, 3-butyltetrahydro-5-methyl acetate, ethyl-3-hydroxy-3-phenyl propionate, cis-3-hexenyl methyl carbonate, anthranillic acid, methyl ester, 10-undecenoic acid, 7-octen-2-ol, 2-methyl-6-methylene acetate, 2,6-octadien-1-ol, 3,7-dimethyl formate, 3,7-dimethyl acetate, nonyl alcohol acetate, 2-norpinene-2-ethanol, 6,6-dimethyl acetate, 5,7-octadien-2-ol, 2,6-dimethyl acetate, lauric acid ethyl ester, octanoic acid, p-tolyl ester, 4-methyl benzene methanol acetate, 2-phenoxyethyl isobutyrate, 2-phenoxyethyl propionate, 2-phenyl ethyl acetate, 2-phenyl ethyl benzoate, beta-phenyl ethyl n-butyrate, cinnamic acid, phenethyl ester, phenethyl alcohol formate, beta-phenyl ethyl isobutyrate, 3-pentanol, 3-methyl-1-phenyl acetate, beta-phenyl ethyl phenyl acetate, beta-phenyl ethyl propionate, beta-phenyl ethyl salicylate, dihydro cinnamic acetate, dihydro cinnamic propionate, 2-buten-1-ol-3-methyl acetate, 2-buten-1-ol-3-methyl benzoate, 6-octen-1-ol-3,7-dimethyl acetate, 6-octen-1-ol-3,7-dimethyl butyrate, 6-octen-1-ol-3,7-dimethyl formate, 6-octen-1-ol-3,7-dimethyl isobutyrate, cyclohexane-1-methanol, alpha, 3,3-trimethyl acetate, 9-decen-1-yl acetate, methyl phenyl carbinyl acetate, methyl phenyl carbinyl propionate, 3-cyclohexene-1-methanol, alpha, alpha, 4-trimethyl acetate, 3-octanol, 3,7-dimethyl-2-octanol, 2,6-dimethyl acetate, 3,5,5-trimethyl hexyl acetate, 3,6-dimethyl-beta-resorcyclic acid methyl ester, 2-tertiary-butyl-cyclohexanyl acetate, cis-3-hexenyl acetate, cis-3-hexen-1-yl isobutyrate, para-tertiary-butyl-cyclohexyl acetate, 2-methyl butyl salicylate, and n-amyl salicylate.

8. The solid complex of claim 1 or 2 wherein the flavor or fragrance molecule is selected from the group consisting of 10-undecen-1-ol, alpha-n-amyl cinnamyl alcohol, 1-octen-3-ol, para-methoxy benzyl alcohol, alpha-3,3-trimethyl cyclohexane-1-methanol, para-isopropyl cyclohexanol, 2-ethyl-4-(2,2,3-trimethyl-3-cyclopenten-1-yl)-2-buten-1-ol, 3,7-dimethyl-6-octen-1-ol, phenoxy acetaldehyde, para-cymen-7-ol, 3,7-dimethyl-6-octen-3-ol, 3,7-dimethyl-1-octanol, 2-methyl-4-phenyl-2-butanol, 2,4-dimethyl-3-cyclohexene-1-methanol, 3,7-dimethyl-2,6-octadien-1-ol, o,m,p-methyl phenyl ethanol, 3-hexen-1-ol, beta-methyl phenyl ethyl alcohol, 3,7-dimethyl-1,7-octanediol, alpha-isobutyl phenethyl alcohol, 3,4,5,6,6-pentamethyl-2-heptanol, 2,6-dimethyl heptan-6-ol, 2,6-dimethyl-7-octen-2-ol, 5-(2,6,6-trimethyl-2-cyclohexen-1-yl)-4-penten-3-one, 3-methyl-4-(2,6,6-trimethyl-1-cyclohexen-1-yl)-3-buten-2-one, 2,6-dimethyl-3,5-octadien-2-ol, 2-methyl-6-methylene-7-octen-2-ol, 3,7-dimethyl-2,6-octadien-1-ol, 2,6-dimethyl-5,7-octadien-2-ol, alpha,alpha-4-trimethyl benzene ethanol, 4-tertiary butyl cyclohexanol, 3-methyl-5-phenyl-1-pentanol, 2-benzyl-m-dioxan-5-ol, 2-phenyl ethyl alcohol, 3-methyl-1-phenyl-3-pentanol, 3,7-dimethyl-6-octen-1-ol, 9-decen-1-ol, alpha,alpha-4-trimethyl-3-cyclohexene-1-methanol, 3,7-dimethyl-3-octanol, 2,6-dimethyl-2-octanol, and 2-tertiary-butyl cyclohexanol.

9. A laundry product that contains the solid complex of claim 1 or 2.

10. A solid food product that contains the solid complex of claim 1 or 2.

11. A solid cleaning product that contains the solid complex of claim 1 or 2.

12. A solid cleaning product consisting essentially of:
a substantially linear flavor or fragrance molecule, the flavor or fragrance molecule having a backbone of at least 5 atoms in length;
urea wherein the urea provides a protective complex around the substantially linear flavor or fragrance molecule; and
further contains an oxidizing agent.

13. A method for providing a flavor or fragrance molecule with a protective coating comprising:
providing urea in an amount sufficient to provide a protective coating;
providing a solvent;
providing a substantially linear flavor or fragrance molecule having a backbone of greater than or equally to five atoms;
admixing said urea, solvent and flavor or fragrance molecule;
removing said solvent and recovering said flavor or fragrance molecule with protective urea coating.

14. The method of claim 13 wherein the flavor or fragrance molecule with the protective urea coating is recovered by filtration.

15. The method of claim 13 wherein the flavor or fragrance molecule with the protective urea coating is recovered by distillation.

16. The process of claim 13 wherein the solvent is an alcohol.

17. The process of claim 16 wherein the alcohol is methanol.

* * * * *